United States Patent [19]

Smith et al.

[11] Patent Number: 4,666,922
[45] Date of Patent: May 19, 1987

[54] METHOD FOR MODULATING THE IMMUNE RESPONSE

[75] Inventors: Sidney R. Smith, Ridgewood; Marvin I. Siegel, Woodbridge, both of N.J.

[73] Assignee: Schering Corporation, Kenilworth, N.J.

[21] Appl. No.: 839,308

[22] Filed: Mar. 13, 1986

Related U.S. Application Data

[63] Continuation-in-part of Ser. No. 746,149, Jun. 18, 1985, abandoned, which is a continuation-in-part of Ser. No. 631,372, Jul. 16, 1984, abandoned.

[51] Int. Cl.$^4$ .................. A61K 31/44; A61K 31/495; A61K 31/505; A61K 31/535
[52] U.S. Cl. .................................... 514/335; 514/227; 514/255; 514/256; 514/334

[58] Field of Search ............... 514/227, 255, 256, 334, 514/335

[56] References Cited

U.S. PATENT DOCUMENTS 4,452,800  6/1984  Sherlock .............................. 546/122

FOREIGN PATENT DOCUMENTS

54154/83  3/1976  Japan .

*Primary Examiner*—Stanley J. Friedman
*Attorney, Agent, or Firm*—James R. Nelson; Stephen I. Miller; Gerald S. Rosen

[57] ABSTRACT

There is disclosed a method for immunomodulation employing as active agents certain substituted 1,8-naphthyridines and 1,5,8-azanaphthyridines.

19 Claims, No Drawings

METHOD FOR MODULATING THE IMMUNE RESPONSE

This application is a continuation-in-part of U.S. application Ser. No. 746,149, filed June 18, 1985, which in turn is a continuation-in-part of U.S. application Ser. No. 631,372 filed July 16, 1984, both now abandoned.

BACKGROUND OF THE INVENTION

The present invention relates to the use of certain naphthyridine compounds in modulating, i.e. potentiating or suppressing, the immune response.

Japanese Pat. No. 54152/83 discloses various naphthyridine derivatives which allegedly possess analgesic, anti-inflammatory, central nervous system depressant and diuretic effects. U.S. Pat. No. 4,452,800 discloses various salts of 3-(n-butyl)-4-hydroxy-1-phenyl-1,8-naphthyridine-2-(1H)-one. U.S. Pat. Nos. 4,492,702 and 4,551,463 discloses the use of various naphthyridine derivatives in treating allergic reactions and in treating and preventing ulcers in mammals. There is no indication in any of these references that such compounds may provide immunomodulating activity.

SUMMARY OF THE INVENTION

The present invention is drawn to a method of modulating the immune response in a mammal which comprises administering a therapeutically effective amount to the mammal of a compound having the structural formula I:

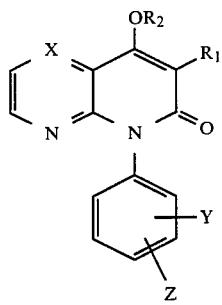

wherein
X is CH or N;
Y is hydrogen, hydroxy, benzyloxy, amino, sulfamyl, halogen, nitro, alkyl having from 1 to 6 carbon atoms, alkoxy having from 1 to 6 carbon atoms, carboxylic acyl having from 2 to 6 carbon atoms, alkyl-$S(O)_m$— having from 1 to 6 carbon atoms wherein m is 0, 1 or 2, trifluoromethyl, trifluoromethylthio, or COOA wherein A is hydrogen, alkyl having from 1 to 6 carbon atoms or a cation derived from a pharmaceutically acceptable metal or an amine;
Z is hydrogen, hydroxy, halogen, alkyl having from 1 to 6 carbon atoms, alkoxy having from 1 to 6 carbon atoms, hydroxyalkyl having from 1 to 6 carbon atoms, or carboxylic acyloxy having from 2 to 6 carbon atoms;
$R_1$ is alkenyl having from 2 to 10 carbon atoms, alkynyl having from 2 to 10 carbon atoms, cycloalkyl having from 3 to 7 carbon atoms, cycloalkenyl having from 5 to 8 carbon atoms, 2-, 3- or 4-pyridyl, 2-,4- or 5-pyrimidyl, 2- or 3-thienyl, 2- or 3-furanyl, carboxylic acyl having from 2 to 6 carbon atoms, or alkyl having from 1 to 10 carbon atoms which may be substituted with —COOH, hydroxy, halogen, alkoxy having from 1 to 6 carbon atoms, phenyl, 2-, 3- or 4-pyridyl, 2-, 4- or 5-pyrimidyl, 2- or 3-thienyl, 2- or 3-furanyl, carboxylic acyl having from 2 to 6 carbon atoms, cycloalkyl having from 3 to 7 carbon atoms or carboxylic acyloxy having from 1 to 6 carbon atoms;
$R_2$ is hydrogen, alkenyl having from 3 to 8 carbon atoms, alkynyl having from 3 to 8 carbon atoms, carboxylic acyl having from 1 to 6 carbon atoms, alkyl having from 1 to 6 carbon atoms, $R_aR_bN(CH_2)_n$—(wherein $R_a$ and $R_b$ are hydrogen, alkyl having from 1 to 6 carbon atoms or may be joined to complete a piperidine, morpholine, piperazine or pyrrolidine ring and n is an integer of from 2 to 6), hydroxyalkyl having from 2 to 6 carbon atoms, dihydroxyalkyl having from 2 to 6 carbon atoms, hydroxyalkoxyalkyl having from 2 to 8 carbon atoms, or a cation derived from a pharmaceutically acceptable metal or an amine.

These are the compounds disclosed in U.S. Pat. Nos. 4,492,702, 4,551,463 and 4,452,800.

The preferred value for X is CH.

The preferred values for Y are hydrogen, methoxy, trifluoromethyl, methylthio; the more preferred value is hydrogen.

The preferred values for Z are hydrogen and methyl.

The peferred values for $R_1$ are n-alkyl having from 3 to 5 carbon atoms, alkenyl from 3 to 4 carbon atoms, omega-hydroxyalkyl having 2 to 4 carbon atoms, and omega-carboxylicacyloxyalkyl having from 6 to 9 carbon atoms; the most preferred values are n-butyl, propen-2-yl, 2-hydroxyethyl, 3-hydroxypropyl and 4-propanoyloxybutyl.

The preferred values for $R_2$ are hydrogen, carboxylic acyl of from 2 to 4 carbon atoms, hydroxyalkyl of from 2 to 4 carbon atoms, $R_aR_bN(CH_2)_n$— (wherein $R_a$ and $R_b$ are each independently hydrogen or alkyl having from 1 to 6 carbon atoms and n is an integer from 2 to 6 carbon atoms) and the cations derived from sodium, potassium, calcium, ethanolamine, N-methylglucamine, diethanolamine, ethylenediamine, tris-(hydroxymethyl)aminomethane and lysine; the most preferred values are hydrogen, ethanoyl, propanoyl, 2-hydroxyethyl, and the cations derived from sodium, N-methylglucamine and lysine.

One class of compounds useful in the present method are those having the formula II:

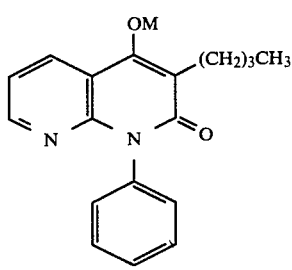

wherein M is a cation derived from a pharmaceutically acceptable non-toxic metal or an amine. The preferred values for M are the cations derived from sodium, potassium, calcium, ethanolamine, N-methylglucamine, diethanolamine, ethylenediamine, tris-(hydroxymethyl) aminomethane and lysine. The more preferred values for M are the cations derived from sodium, N-methylglucamine and lysine.

Preferred compounds for use in the present invention include compounds having the formulae I$_a$–I$_g$:

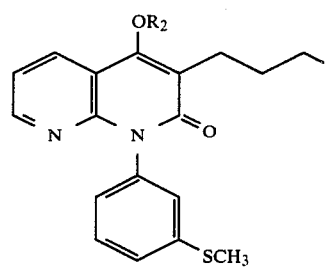

I$_a$

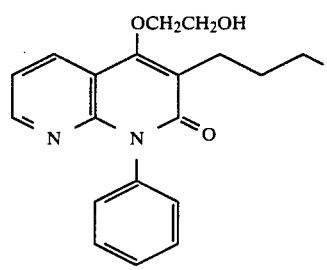

I$_b$

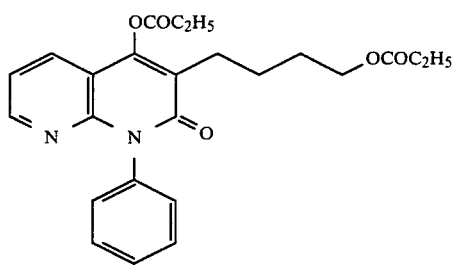

I$_c$

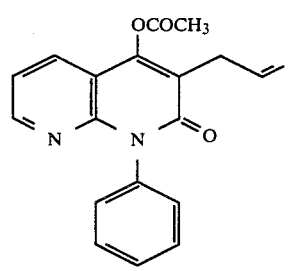

I$_d$

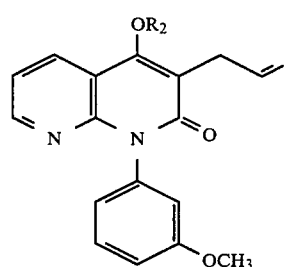

I$_e$

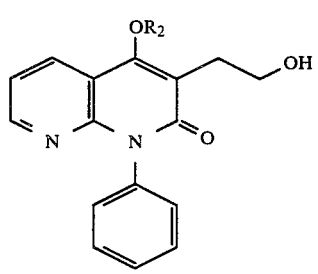

I$_f$

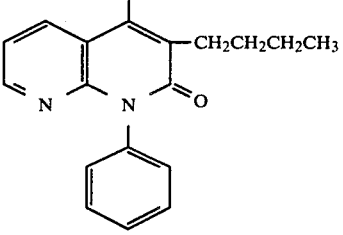

I$_g$ wherein R$^2$ is hydrogen or the sodium cation.

DESCRIPTION OF THE INVENTION

The compounds which are utilized in the method of the invention are substituted 1,8-naphthyridines and 1,5,8-azanaphthyridines and may exist as solvates, for example as hydrates. These compounds include salts formed at the 4-hydroxy group of 3-(n-butyl)-4-hydroxy-1-phenyl-1,8-naphthyridine-2(1H)-one.

The compounds which are utilized in the method of this invention include those disclosed in U.S. Pat. Nos. 4,452,800, 4,492,702, and 4,551,463 and the pharmaceutically acceptable metal or amino salts of the compound 3-(n-butyl)-4-hydroxy-1-phenyl-1,8-naphthyridine-2(1H)-one which is disclosed in Japanese patent public disclosure (Kokai) No. 116495/77, Sept. 29, 1977, now Japanese Pat. No. 54152/83. These compounds may be prepared by methods described in U.S. Pat. Nos. 4,452,800, 4,492,702 and 4,551,463, the disclosures of which are incorporated herein by reference for this purpose.

The sodium and potassium salts of this invention can be readily prepared by reacting the appropriate compound, e.g., 3-(n-butyl)-4-hydroxy-1-phenyl-1,8-naphthyridine-2(1H)-one, with respectively, sodium hydroxide solution or potassium hydroxide solution.

The amine and amino acid salts can be prepared by reacting the appropriate amine or amino acid with the desired hydroxylated compound, e.g. 3-(n-butyl)-4-hydroxy-1-phenyl-1,8-naphthyridine-2(1H)-one, in a compatable organic solvent, e.g. methanol.

The calcium salt can be prepared by reaction of the sodium salt with calcium chloride solution.

The aluminum, bismuth, chromium, copper, iron, magnesium, manganese and zinc salts of this invention can be prepared by methods known to those of skill in the art.

When utilized herein and in the appended claims the below listed terms, unless specified otherwise, are defined as follows:

halogen—fluorine, chlorine, bromine and iodine;

alkyl—straight and branched carbon chains containing from 1 to 10 carbon atoms; hydroxyalkyl and dihydroxyalkyl having from 2 to 6 carbons—hydroxyalkyl and dihydroxyalkyl groups wherein the hydroxy group(s) is not substituted at the position alpha to the oxygen to which the R$_2$ group is attached.

R$_2$ is alkenyl and alkynyl having from 3 to 8 carbon atoms-alkenyl and alkynyl groups wherein the unsaturation is not at the position alpha to the oxygen to which the R$_2$ group is attached.

Pharmaceutically acceptable metal and amine—metals and amines that are generally recognized as being non toxic, such as sodium, potassium, calcium, aluminum, N-methylglucamine, lysine and the like.

The compounds of formulae I and II can exist in unsolvated as well as solvated forms, including hydrated forms. In general, the solvated forms, with pharmaceutically acceptable solvents such as water, ethanol and the like are equivalent to the unsolvated forms for purposes of the invention.

The compounds are useful in the treatment of autoimmune and other immunological diseases including graft rejection in which T cell proliferation is a contributing factor to the pathogenesis of disease. The effectiveness of these compounds as immunomodulating agents may be demonstrated by the following tests which involve the inhibition of T cell functions using these compounds.

Graft vs. Host Reaction (GVHR)

To induce a GVHR, C57 B1/6XA/J(B6AF1) male mice were injected intraperitoneally with parental (C57B1/6J) spleen cells. 3-(n-Butyl)-4-hydroxy-1-phenyl-1,8-naphthyridine-2(1H)-one sodium salt was then administered orally for 8 days beginning on the day of cell transfer. On the day following the last treatment, body weights were obtained, the animals were sacrificed, and their spleens were excised and weighed. The enlargement of the spleen of the host is a result of a GVHR. To some extent it is the host's own cells which infiltrate and enlarge the spleen although they do this because of the presence of graft cells reacting against the host. The amount of spleen enlargement, splenomegaly, is taken as a measure of the severity of the GVHR.

The GVHR is expressed below as the spleen index, the ratio of the weight of the spleen to the total weight of the animal in the experimental group compared with the same ratio in the control group.

$$\text{spleen index} = \frac{\text{weight of experimental spleen/total body weight}}{\text{weight of control spleen/total body weight}}$$

In carrying out the GVHR the animal in the experimental group is injected with parental cells, cells of the same species but of different genotype, which cause a weight increase of the spleen. The animal in the control group is injected with syngeneic cells, genetically identical cells, which do not cause a weight increase of the spleen. The effectiveness of the sodium salt administered to the mice in the experimental group is measured against a spleen index scale. The scale goes from a spleen index of 1.0 for complete immunosuppression to a spleen index of 2.6 for a lack of immunosuppression.

The sodium salt at 100 mg/kg gave a spleen index of 1.6.

T Cell Mitogenic Responsiveness

Spleen cells were obtained from six to eight week old C57 B1/6J male mice. One million viable spleen cells were cultured in triplicate in microtest II plates in the presence of 1 ug concanavalin A (Con A) or 0.25 ug phytohemagglutinin (PHA) for 72 hr at 37° C. The total volume was 0.2 ml. One microcurie $^3$H-thymidine (specific activity, 2.0 Ci/mmole) was added for the last 16 hr of incubation. The cells were harvested and processed on a mash II harvester. A stock solution of $1 \times 10^{-2}$M of the drug was prepared in distilled water and then diluted with medium to the appropriate concentration. The sodium salt of 3-(n-butyl)-4-hydroxy-1-phenyl-1,8-naphthyridine-2(1H)-one at concentrations of 1 and 10 uM inhibited the proliferative responses of unfractionated murine splenocytes to the T cell mitogens, Con A and PHA.

The compounds of formulas I and II are orally and parenterally effective in the treatment of autoimmune and other immunological diseases including graft rejection at a dosage range of 5 to 250 mg/kg of body weight per day, preferably 25 to 150 mg/kg.

The usual dosage range for the compounds of formulas I and II in a 70 kg mammal is an oral dose of about 5 to 250 mg/kg, preferably 25 to 150 mg/kg, in 3 or 4 divided doses. Of course, the dose will be regulated according to the immunological disease being treated, the judgement of the attending clinician depending on factors such as the degree and severity of the disease state and age and general condition of the patient being treated.

To treat immunological diseases, the active compounds of formulas I and II can be administered in unit dosage forms such as tablets, capsules, pills, powders, granules, sterile parenteral solutions or suspensions, suppositories and the like. Such dosage forms are prepared according to the standard techniques well known in the art.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 1000 mg according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following examples illustrate the preparation of the compounds used in the methods of this invention as well as pharmaceutical compositions containing the compounds. All temperatures are in degrees Celsius. Reference is made to U.S. Pat. Nos. 4,452,800, 4,492,702 and 4,551,463 for other examples of the preparation of compounds employed in the method of the invention.

EXAMPLE 1

3-(n-Butyl)-4-Hydroxy-1-Phenyl-1,8-Naphthyridine-2(1H)-One Sodium Salt

Add 57.9 ml of 1N sodium hydroxide aqueous solution to a stirred suspension of 17.05 g of 3-(n-butyl)-4-hydroxy-1-phenyl-1,8-naphthyridine-2(1H)-one and 140 ml of water. Stir for one hour at room temperature, cool in an ice bath and filter. Lyophilize the clear filtrate overnight to give the title compound as a monohydrate. It is a cream colored powder, m.p. 240°–260° (decomposition).

Prepare the corresponding potassium salt as a monohydrate by the process of Example 1 by replacing the sodium hydroxide aqueous solution with an equivalent amount of potassium hydroxide aqueous solution. The lyophilized potassium salt has a melting point of 215°–225°.

EXAMPLE 2

3-(N-Butyl)-4-Hydroxy-1-Phenyl-1,8-Naphthyridine-2(1H)-One Ethanolamine Salt

Add 0.65 g of ethanolamine to 3-(n-butyl)-4-hydroxy-1-phenyl-1,8-naphthyridine-2(1H)-one in 100 ml of methanol. Remove the solvent in vacuo and add ethyl acetate to precipitate the title compound as a colorless salt, m.p. 228°–234°.

Prepare the following amine salts by the process of Example 2 by replacing the ethanolamine with the corresponding amine:
3-(n-butyl)-4-hydroxy-1-phenyl-1,8-naphthyridine-2(1H)-one N-methylglucamine salt, melting point 181°–206°.
3-(n-butyl)-4-hydroxy-1-phenyl-1,8-naphthyridine-2(1H)-one diethanolamine salt, melting point 160°–190°.
3-(n-butyl)-4-hydroxy-1-phenyl-1,8-naphthyridine-2(1H)-one ethylenediamine salt, melting point 158°–171°.

EXAMPLE 3

3-(n-Butyl)-4-Hydroxy-1-Phenyl-1,8-Naphthyridine-2(1H)-One Calcium Salt

Treat a solution of 1 g (3 mmoles) of the compound of Example 1 herein with 1.5 ml of 1N calcium chloride solution (1.5 mmoles). Filter the resulting cloudy solution and allow to stand until a precipitate forms. Filter and wash with acetone. Recover the title compound from water or acetone-water as a pentahydrate which is a colorless powder, m.p. >350°.

In the following examples of dosage forms, the term "Active Compound" represents any of the compounds of formulas I and II above such as the compounds prepared in the foregoing Examples 1–3; 3-(n-butyl)-4-hydroxy-1-(3-methylthiophenyl)-1,8-naphthyridin-2-(1H)-one; 3-(n-butyl)-4-hydroxy-1-phenyl-1,8-naphthyridin-2-(1H)-one; 4-acetoxy-1-phenyl-3-(2-propenyl)-1,8-naphthyridin-2-(1H)-one; 4-hydroxy-1-phenyl-3-(2-propenyl)-1,8-naphthyridin-2-(1H)-one; 4-hydroxy-1-(3-methoxyphenyl)-3-(2-propenyl)-1,8-naphthyridin-2(1H)-one ; 1-phenyl-4-propionyloxy-3-(4-propionyloxybutyl)-1,8-naphthyridin-2(1H)-one; 3-(2-hydroxyethyl)-4-hydroxy-1-phenyl-1,8-naphthyridin-2(1H)-one; 3-(n-butyl)-4-(2-hydroxyethoxy)-1-phenyl-1,8-naphthyridin-2(1H)-one; 4-hydroxy-1-phenyl-3-(2-pyridyl)-1,8-naphthyridin-2(1H)-one; and 3-(n-butyl)-4-

[2-(2-hydroxyethoxy)ethoxy]-1-phenyl-1,8-naphthyridin-2(1H)-one.

Pharmaceutical Dosage Form Examples

The active compounds used in the pharmaceutical dosage form examples are those of structural formula I.

Example A

| | Tablets | | |
|---|---|---|---|
| No. | Ingredient | mg/tablet | mg/tablet |
| 1. | Active compound | 100 | 500 |
| 2. | Lactose USP | 122 | 113 |
| 3. | Corn, Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixture for 10–15 minutes. Granulate the mixture with Item No. 3. Mill the damp granules through a coarse screen (e.g., ¼") if needed. Dry the damp granules. Screen the dried granules if needed and mix with the Item No. 4 and mix for 10–15 minutes. Add Item No. 5 and mix for 1–3 minutes. Compress the mixture to appropriate size and weight on a suitable tablet machine.

Example B

| | Capsules | | |
|---|---|---|---|
| No. | Ingredient | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

Example C

| Parenteral | | |
|---|---|---|
| Ingredient | mg/vial | mg/vial |
| Active Compound Sterile Powder | 100 | 500 |

Add sterile water for injection or bacteriostatic water for injection for reconstruction.

Example D

| | Injectable | | |
|---|---|---|---|
| No. | Ingredient | mg/vial | mg/vial |
| 1. | Active Compound | 100 | 500 |
| 2. | Methylparaben | 1.8 | 1.8 |
| 3. | Propylparaben | 0.2 | 0.2 |
| 4. | Sodium Bisulfite | 3.2 | 3.2 |
| 5. | Disodium Edetate | 0.1 | 0.1 |
| 6. | Sodium Sulfate | 2.6 | 2.6 |
| 7. | Water for Injection q.s. ad | 1.0 ml | 1.0 ml |

Method of Manufacture

1. Dissolve parabens in a portion (85% of the final volume) of the water for injection at 65°–70° C.
2. Cool to 25°–35° C. Charge and dissolve the sodium bisulfite disodium edetate and sodium sulfate.
3. Charge and dissolve drug.
4. Bring the solution to final volume by added water for injection.
5. Filter the solution through 0.22 membrane and fill into appropriate containers.
6. Terminally sterilize the units by autoclaving.

What is claimed is:

1. A method of modulating the immune response in a mammal which comprises administering to a mammal in need of such treatment a therapeutically effective amount of a compound having the structural formula I

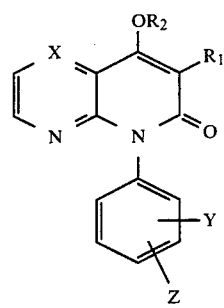

wherein X is CH or N;

Y is hydrogen, hydroxy, benzyloxy, amino, sulfamyl, halogen, nitro, alkyl having from 1 to 6 carbon atoms, alkoxy having from 1 to 6 carbon atoms, carboxylic acyl having from 2 to 6 carbon atoms, alkyl—$S(O)_m$— having from 1 to 6 carbon atoms wherein m is 0, 1 or 2, trifluoromethyl, trifluoromethylthio, or COOA wherein A is hydrogen, alkyl having from 1 to 6 carbon atoms or a cation derived from a pharmaceutically acceptable metal or an amine;

Z is hydrogen, hydroxy, halogen, alkyl having from 1 to 6 carbon atoms, alkoxy having from 1 to 6 carbon atoms, hydroxyalkyl having from 1 to 6 carbon atoms, or carboxylic acyloxy having from 2 to 6 carbon atoms;

$R_1$ is alkenyl having from 2 to 10 carbon atoms, alkynyl having from 2 to 10 carbon atoms, cycloalkyl having from 3 to 7 carbon atoms, cycloalkenyl having from 5 to 8 carbon atoms, 2-, 3- or 4-pyridyl, 2-,4- or 5-pyrimidyl, 2- or 3-thienyl, 2- or 3-furanyl, carboxylic acyl having from 2 to 6 carbon atoms or alkyl having from 1 to 10 carbon atoms which may be substituted with —COOH, hydroxy, halogen, alkoxy having from 1 to 6 carbon atoms, phenyl, 2-, 3- or 4-pyridyl, 2-, 4- or 5-pyrimidyl, 2- or 3-thienyl, 2- or 3-furanyl, carboxylic acyl having from 2 to 6 carbon atoms, cycloalkyl having from 3 to 7 carbon atoms or carboxylic acyloxy having from 1 to 6 carbon atoms;

$R_2$ is hydrogen, carboxylic acyl having from 1 to 6 carbon atoms, alkenyl having from 3 to 8 carbon atoms, alkynyl having from 3 to 8 carbon atoms, alkyl having from 1 to 6 carbon atoms, $R_aR_bN(CH_2)_n$— (wherein $R_a$ and $R_b$ are hydrogen, alkyl having from 1 to 6 carbon atoms or may be joined to complete a piperidine, morpholine, piperazine or pyrrolidine ring and n is an integer of from 2 to 6), hydroxyalkyl having from 2 to 6 carbon atoms, dihydroxyalkyl having from 2 to 6 carbon atoms, hydroxyalkoxyalkyl having from 2 to 8 carbon atoms, or a cation derived from a pharmaceutically acceptable metal or an amine.

2. The method defined in claim 1 wherein X is CH.

3. The method defined in claim 2 wherein Y is selected from hydrogen, methoxy, trifluoromethyl or methylthio and Z is selected from hydrogen or methyl.

4. The method defined in claim 3 wherein $R_1$ is selected from n-alkyl having from 3 to 5 carbon atoms, alkenyl having from 3 to 4 carbon atoms, omegahydroxyalkyl having from 2 to 4 carbon atoms and omega-carboxylicacyloxyalkyl having from 6 to 9 carbon atoms.

5. The method defined in claim 4 wherein $R_2$ is selected from hydrogen, carboxylic acyl of from 2 to 4 carbon atoms, hydroxyalkyl of from 2 to 4 carbon atoms, $R_aR_bN(CH_2)_n$— in which $R_a$ and $R_b$ each independently represent hydrogen or alkyl of from 1 to 6 carbon atoms and n represents an integer of from 2 to 6, and cations derived from sodium, potassium, calcium, ethanolamine, N-methylglucamine, diethanolamine, ethylenediamine, tris-(hydroxymethyl)aminomethane and lysine.

6. The method defined in claim 1 wherein the compound is 3-(n-butyl)-4-hydroxy-1-(3-methylthiophenyl)-1,8-naphthyridin-2(1H)-one.

7. The method defined in claim 1 wherein the compound is 4-acetoxy-1-phenyl-3-(2-propenyl)-1,8-naphthyridin-2(1H)-one.

8. The method defined in claim 1 wherein the compound is 3-(n-butyl)-4-(2-hydroxyethoxy)-1-phenyl-1,8-naphthyridin-2(1H)-one.

9. The method defined in claim 1 wherein the compound is 4-hydroxy-3-(2-propenyl)-1-phenyl-1,8-naphthyridin-2(1H)-one.

10. The method defined in claim 1 wherein the compound is 4-hydroxy-1-(3-methoxyphenyl)-3-(2-propenyl)-1,8-naphthyridin-2(1H)-one.

11. The method defined in claim 1 wherein the compound is 1-phenyl-4-propionyloxy-3-(4-propionyloxybutyl)-1,8-naphthyridin-2(1H)-one.

12. The method defined in claim 1 wherein the compound is 4-hydroxy-3-(2-hydroxyethyl)-1-phenyl-1,8-naphthyridin-2(1H)-one.

13. The method defined in claim 1 wherein said compound is of the formula

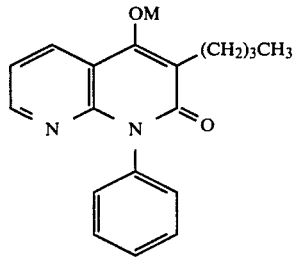

II wherein M is a cation derived from a pharmaceutically acceptable metal, an amine or amino acid.

14. The method defined in claim 13 wherein M is sodium.

15. The method defined in claim 13 wherein M is potassium.

16. The method defined in claim 13 wherein M is calcium.

17. The method defined in claim 13 wherein M is selected from ethanolamine, N-methylglucamine, diethanolamine, ethylenediamine, tris-(hydroxymethyl) aminomethane, or lysine.

18. The method defined in claim 1 wherein the compound is administered orally.

19. The method according to claim 13 wherein the compound is administered orally.

* * * * *